(12) United States Patent  (10) Patent No.: US 7,761,932 B2
Faussett et al.  (45) Date of Patent: Jul. 27, 2010

(54) EAR PROTECTION DEVICE

(75) Inventors: Spring S. Faussett, Mountlake Terrace, WA (US); Adam M. Faussett, Mountlake Terrace, WA (US); Kevin W. Shimasaki, Woodinville, WA (US); John Malmanger, Burien, WA (US)

(73) Assignee: Polar Fusion LLC, Kent, WA (US)

( * ) Notice: Subject to any disclaimer, the term of this patent is extended or adjusted under 35 U.S.C. 154(b) by 1392 days.

(21) Appl. No.: 10/510,616

(22) PCT Filed: Apr. 8, 2003

(86) PCT No.: PCT/US03/10903

§ 371 (c)(1),
(2), (4) Date: Aug. 4, 2005

(87) PCT Pub. No.: WO03/086124

PCT Pub. Date: Oct. 23, 2003

(65) Prior Publication Data

US 2006/0015989 A1  Jan. 26, 2006

Related U.S. Application Data

(60) Provisional application No. 60/370,918, filed on Apr. 8, 2002, provisional application No. 60/401,990, filed on Aug. 7, 2002.

(51) Int. Cl.
*A42B 1/06* (2006.01)

(52) U.S. Cl. ......................................................... 2/209

(58) Field of Classification Search ...................... 2/209, 2/174, 208, 423; 381/388, 379, 374, 370–372
See application file for complete search history.

(56) References Cited

U.S. PATENT DOCUMENTS

| 2,899,683 | A | 8/1959 | Wadsworth |
| 5,357,585 | A | 10/1994 | Kumar ....................... 381/373 |
| 5,673,438 | A | 10/1997 | Lambert ......................... 2/209 |
| 5,835,609 | A | 11/1998 | LeGette et al. .............. 381/187 |
| 6,332,223 | B1 | 12/2001 | Le Gette et al. ................. 2/209 |
| 6,499,146 | B2 | 12/2002 | Bavetta et al. .................. 2/209 |
| 6,502,247 | B2 | 1/2003 | Le Gette et al. ................. 2/209 |
| 6,502,248 | B2 | 1/2003 | LeGette et al. .................. 2/209 |

FOREIGN PATENT DOCUMENTS

WO  WO 94/09734 A1  11/1994

*Primary Examiner*—Tejash Patel
(74) *Attorney, Agent, or Firm*—Seed IP Law Group PLLC

(57) ABSTRACT

An ear protection device (18) that includes a pair of ear protectors (23), each ear protector (23) having a pocket (64) associated therewith that is sized and shaped to be received over the top of the user's ear to support the device (18) on the ear; and a band (22) connected to the pair of ear protectors (23), the band (22) formed of lightweight resilient material and configured to position the ear covers in alignment with the user's ears and with the pockets (64) positioned over the tops of the respective ears. A selectively positionable door (30) is provided on the exterior of each ear protector (23) to cover and uncover an opening in each protector to facilitate the passage of sound to the user's ear through the ear cover when the door (30) is in an opened position.

25 Claims, 9 Drawing Sheets

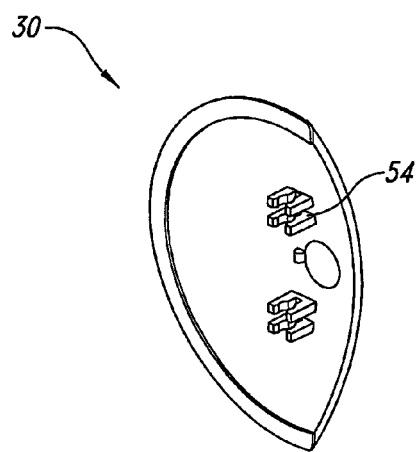
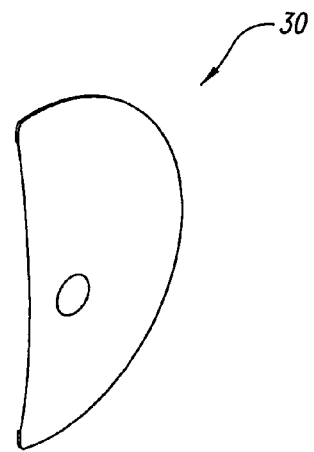
FIG. 8A    FIG. 8B
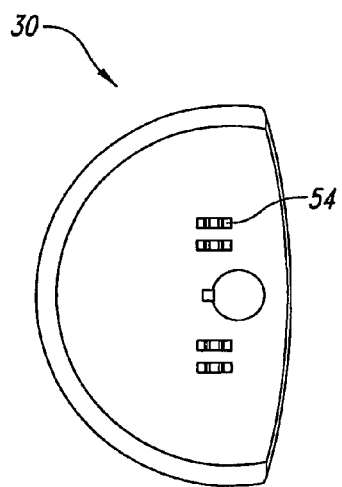
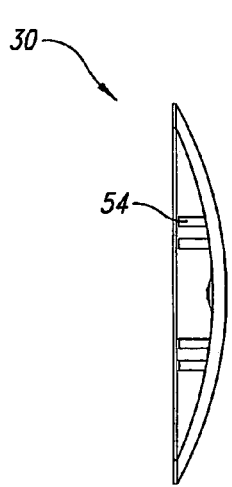
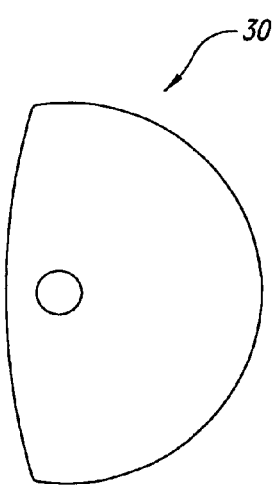
FIG. 8C    FIG. 8D    FIG. 8E

EAR PROTECTION DEVICE

BACKGROUND OF THE INVENTION

1. Field of the Invention

The present invention is directed to a device for protecting the ears of the user, and more particularly to a lightweight ear protection device that is supported by the ears and protects the ears from the elements while facilitating the user's ability to hear.

2. Description of Related Art

Conventionally, ear muffs and the like have been provided with ear pieces at each end of a headband, with the ear pieces then being worn with the headband put around the top of the head or around the base of the head region of the head. FIG. 1 shows an example a known headband that wraps around the back of the head. Here, the article 10 comprises two ear pieces 16 (with only one being shown in FIG. 1) and a headband 14 clamping the ear pieces 16 at each end to the user's head 12. The headband 14 is constructed of flexible material, for example, a plastic spring material, to provide resilience.

The article 10 is put on the user's head 12 by slightly broadening the space between the ear pieces 16 at the ends of the headband 14 so that the ear pieces 16 are brought in position adjacent the ears 11. When the article 10 is put onto the head 12, it is positioned in such a manner that the ear pieces are pressed onto the user's head 12 and ears 11 by the resilience of the headband 14. In this way, the ears become sandwiched between the head 12 and the ear pieces 16. At the same time, the middle of the headband 14 comes into contact with the neck or collar of the wearer at the base 15 of the head region 20 of the user's head 12.

When this article 10 is used as described above, the ear pieces 16 are pressed to the head 12 as a result of the resilience of the headband 14. However, this structure does not enable active support by the ears 11 because its means of support is tension from the resilient material. In some designs it can be partially supported by the middle part of the headband 14 coming into contact with or riding on the base 15 of the user's head region 20 or the neck 19 or collar 21 at the side of the base 15 of the head region 20.

Unfortunately, when, for example, the headband 14 comes into contact with the neck 19 or collar 21 of the user's clothes, movement of the user's head 12 generates stress in the headband 14, thus stressing the entire structure. As a result, the position of the article 10 is frequently changed, causing noise and discomfort, which affects an individual's ability to concentrate and hear. In addition, the resilience of the tensioned headband 14 forms a sealed cup around the ears, interfering with sound entering into the ear canal. Because there is no active ear support feature, the resilience in the headband 14 must be strong enough to prevent the ear protection device 10 from falling off the head 12, causing unnecessary pressure to be exerted on the ears and the head 12, which can cause discomfort to the user. This discomfort is compounded when the level of sound the user can hear from beneath the ear pieces 16 is diminished. Thus, despite the existence of various types of earmuffs and headbands, there remains a need for an ear protection device having the advantages of the present invention.

BRIEF SUMMARY OF THE INVENTION

The disclosed and claimed embodiments of the invention are directed to an ear protection device that includes a pair of ear protectors, each ear protector having an ear cup sized and shaped to be received over a user's ear, and a pocket associated with the ear cup that is sized and shaped to be received over the top of the user's ear and to support the device on the ear; and a band connected to the pair of ear protectors, the band formed of lightweight resilient material and configured to position the ear covers in alignment with the user's ears and with the pockets positioned over the tops of the respective ears. Ideally, the band is sized and shaped to extend downward below the user's earlobe when worn by the user and to extend behind the user's head to leave an unobstructed space adjacent the top of the user's ear to accommodate glasses and headgear.

In accordance with another aspect of the present invention, the band can be configured to provide sufficient tension to hold the ear protector against the user's head to resist the entry of wind into the user's ear.

In accordance with another aspect of the present invention, each ear protector further includes an inside wall configured to bear against the user's ear, an outside wall adjacent the inside wall and separated by a hollow interior, a first opening formed in the inside wall communicating with the hollow interior and a second opening formed in the outside wall that communicates with the hollow interior; the ear protector further including a cover mounted on the outside wall to selectively cover and uncover the second opening formed in the outside wall. The cover may be hingedly or slidably affixed to the outside wall. Hearing can be further enhanced through the use of active amplifiers.

In accordance with yet another aspect of the foregoing embodiment of the invention, a pocket is formed, preferably of fabric material, that is associated with the ear cup that is sized and shaped to be received over the top of the user's ear. Ideally, the pocket is held in an opened configuration by a ledge or protrusion formed on the ear cup over which the pocket is mounted. In one embodiment the ledge has a crescent shape that follows the curved contour of the ear cup In accordance with another embodiment of the invention, a device for protecting the ears of a user is provided that includes covers for the ears, the covers include a support for holding the covers on the top of the user's ears; a structure for positioning the covers over the ears so the supports are in alignment over the tops of the user's ears; and a structure for selectively covering and uncovering an opening in the ear cover to facilitate the hearing of the user when the covering structure is in an opened position wherein the opening in the ear cover is unobstructed.

In accordance with yet another embodiment of the invention, a lightweight device for protecting the ears of a user and accommodating the use of headgear, including, but not limited to, glasses and hats, is provided. The lightweight device includes first and second ear protectors that are each sized and shaped to be received over a respective ear of the user and further including a support configured to be received over the top of the user's ear to support the device on the user's ear; and a connection member associated with the first and second ear protectors and configured to position the first and second ear protectors adjacent the ears of a user with the supports aligned over the top of the respective ear of the user, the connection member further configured to hold the first and second ear protectors against the head of the user with sufficient force to resist the entry of air between the ear protectors and the user's head when the user is moving through the air. Ideally, the connection member is configured to pass below the user's earlobes and behind the user's head to facilitate the use of headgear on the user's head.

In accordance with another aspect of the foregoing embodiment, an opening is formed in each of the first and second ear protectors to facilitate the passage of sound from outside the ear protectors to the user's ear, and further comprising a door mounted to each ear protector, each door configured to be selectively openable to facilitate the hearing of the user and closable to cover the opening in the ear protector. Ideally, the door is hingedly attached to the ear protector to swing forward into an opened configuration in a manner to deflect moving air away from the opening in the ear protector.

In accordance with another aspect of the foregoing embodiment, the support on the ear protector comprises a fabric pocket sized and shaped to be slidably received over the top of the user's ear, each ear protector further comprising a ledge formed thereon that is sized and shaped to hold the pocket open to facilitate placement of the ear protector on the top of the user's ear.

In accordance with another aspect of the present invention, there is provided an ear protection device that includes at least one ear cup with an ear rest that rests on top of an ear and a headband having flexibility and resilience to position the at least one ear cup in alignment with the user's ear.

In accordance with another aspect of the present invention, the components of the ear protection device are formed with semi-rigid material in a generally semi-spherical configuration, with each ear cup having a concave inner surface. The internal elements consist of suitable materials to create comfortable warmth and protection for the ears. The ear cups are constructed or covered with an insulating material such as fabric, which by design requires minimal material and therefore reduces the amount of fabric and related sewing required for construction. The device of the present invention may incorporate an acoustic device such as audio speakers, sound amplifiers, or similar type devices to create a combination ear protection device and headphone.

In accordance with a further aspect of the present invention, the ear protection device includes an acoustic feature that acts as a passive amplifier by directing sound waves to travel through a path into the ear, allowing for hearing to be enhanced and minimally obstructed.

As will be readily appreciated from the foregoing, the ear protection device features components that make the device easy and comfortable to wear while warming the ears. It is designed to utilize passive amplification of sound, and it has minimally obstructed hearing. The ear cups are pressed against the ear with a small amount of tension from a slightly resilient headband. The ear cups are provided with ear rests having a support to come into contact with the top portion of the ear. When the ear cups are covered with a material such fabric, the pocket combined with the ear rest and the resilience of the headband work together to ensure stability in wearing the ear protection device.

BRIEF DESCRIPTION OF THE SEVERAL VIEWS OF THE DRAWING(S)

The foregoing features and advantages of the present invention will be more readily appreciated as the same become better understood from the accompanying drawings in which like elements have the same reference numbers, wherein:

FIGS. 8A-8E are right and left isometric views, a back view, a side view and a front view of a door, respectively.

DETAILED DESCRIPTION OF THE INVENTION

Figure 1:
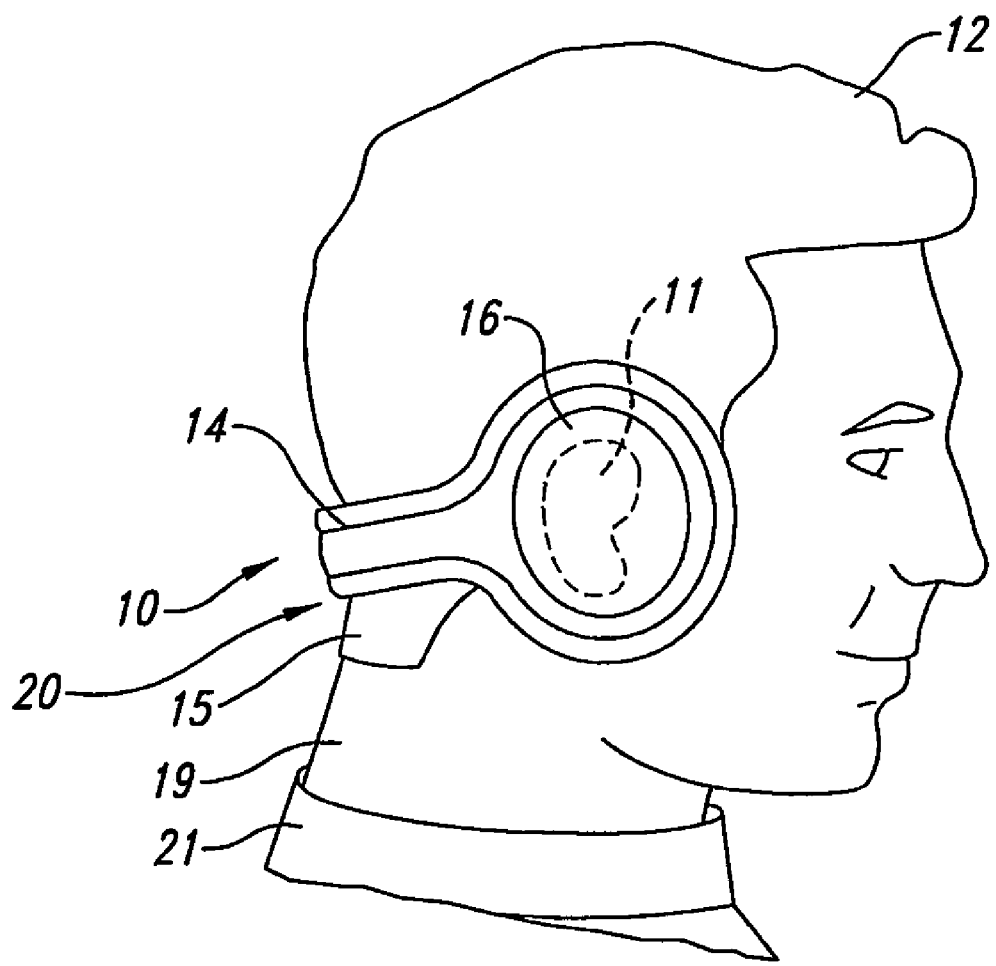
FIG. 1 is a side view of a prior device.
Figure 2:
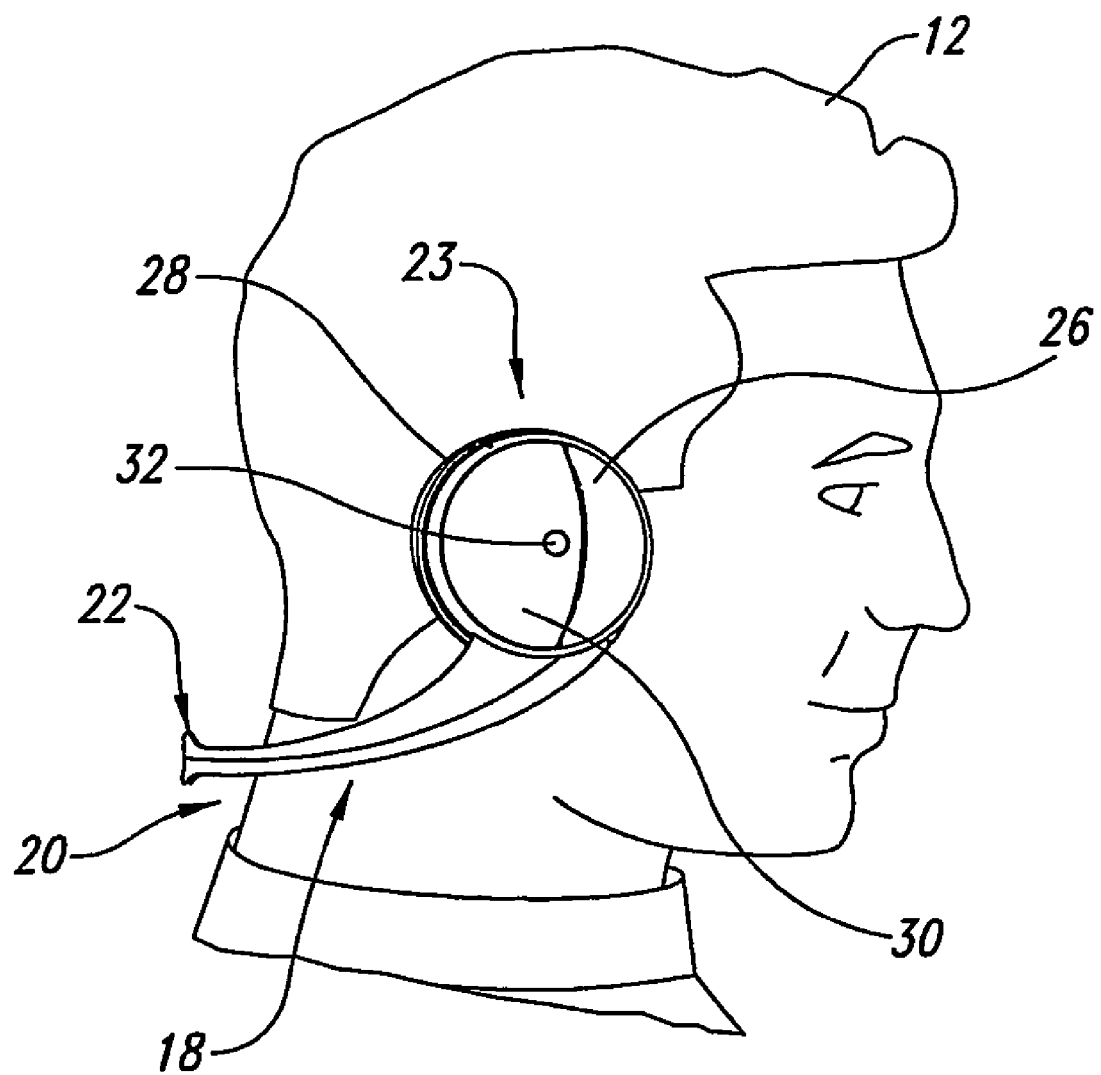
FIG. 2 is a side view of one embodiment of an ear protection device formed in accordance with the present invention.

Referring initially to FIG. 2, shown therein is a side view illustration of a first embodiment of the ear protection device 18 formed in accordance with the present invention. The device 18, shown on the head 12 of a user, has ear protectors 23 connected to or integrally formed with a headband 22 that positions the ear protectors 23 adjacent to and in alignment with the ears (not shown in this view) of the user.

Figure 3:
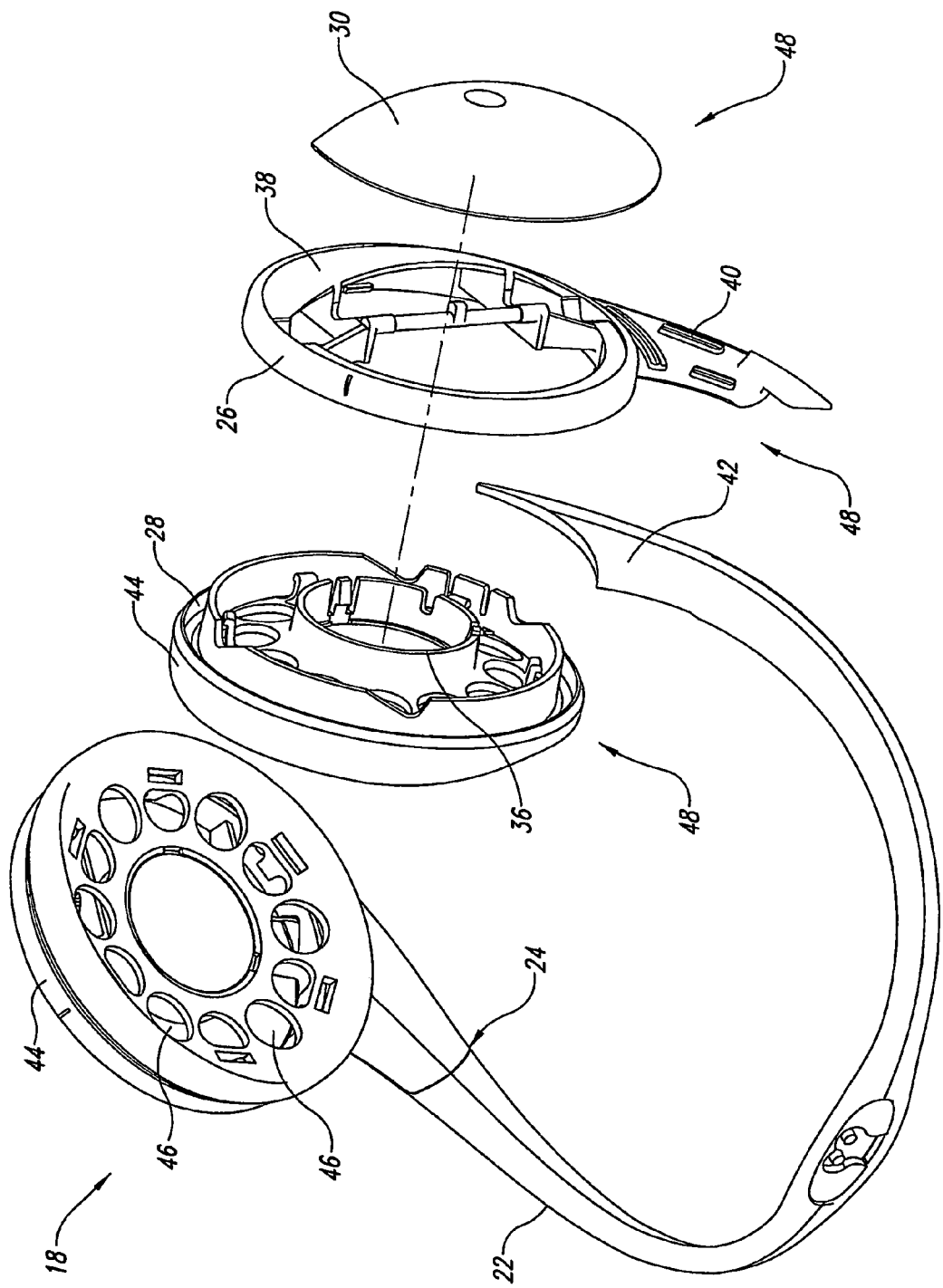
FIG. 3 is an exploded isometric projection of the ear protection device of FIG. 2.
Figure 4:
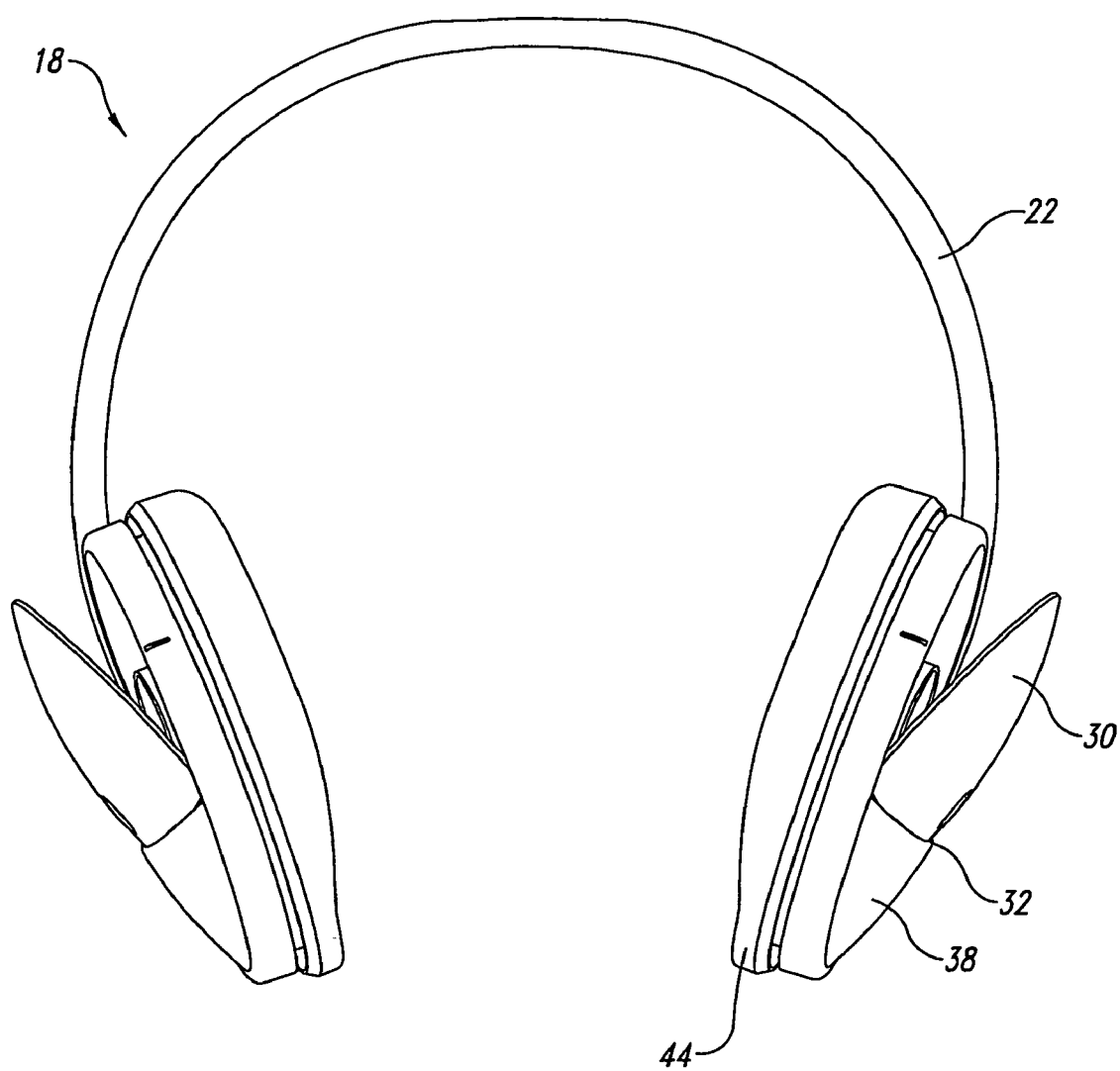
FIG. 4 is a top view of the ear protection device of FIG. 3.
Figure 5:
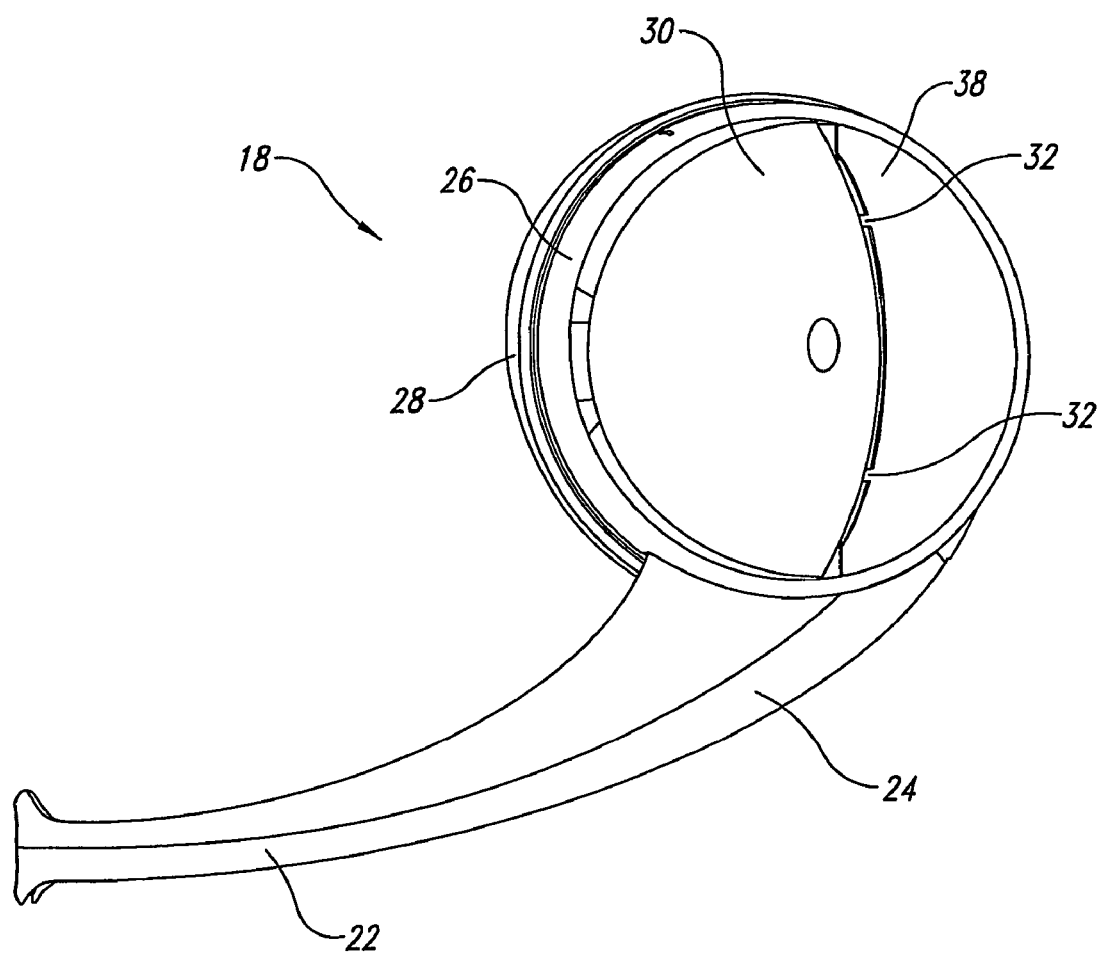
FIG. 5 is an enlarged side view of the ear protection device of FIG. 3.

As shown more clearly in FIG. 3, the device 18 includes outer ear frames 26 that are either connected to the frame 22 by an interlocking joint 24 or are integrally formed therewith and inner ear cups 28 attached to the ear frames 26. The headband 22 is formed to have a semi-flat, elliptical shape, which in one embodiment connects to the outer ear frame 26 through the interlocking joint 24. The joint 24 includes connectors 40 and 42. The interlocking joint 24 is secured when the connectors 40 and 42 are fused together through a process such as gluing or sonic welding.

The headband frame 22 is formed in a curved shape to fit the shape of a typical individual's head, and more particularly to fit the shape of the base 15 of the head region 20 of an individual's head 12. The overall shape of the headband 22 is approximately that of an omega ($\Omega$). As shown in FIG. 2, the headband frame 22 is formed to curve in a lower direction overall so as to approximately run along the lower ends of ears, known commonly as the lobe of the ears. More particularly, the headband 22 is sized and shaped to extend downward below the user's earlobe when worn by the user and to extend behind the user's head 12 to leave an unobstructed space adjacent the top of the user's ear to accommodate the use of headgear such as glasses, hats and helmets.

Referring to FIGS. 3-8, the ear frame 26 is formed to have a concave-shaped outer wall 38 that is, in this embodiment, substantially semi-circular in nature. It is to be understood that the shape can be other than semi-circular. This built in concave shape is aerodynamically designed so that moving air is directed around the outer wall 38 of the ear protection device 18 rather than directed toward the user's ear. The ear cups 28 are formed with semi-rigid material in a generally spherical configuration, with each ear cup 28 having a concave inside surface 29 and a convex outside surface 31. The ear cups 28 are formed of suitable materials to create comfortable warmth and protection for the ears such as fabric or soft moldable components such as plastic or silicone.

Figure 6:
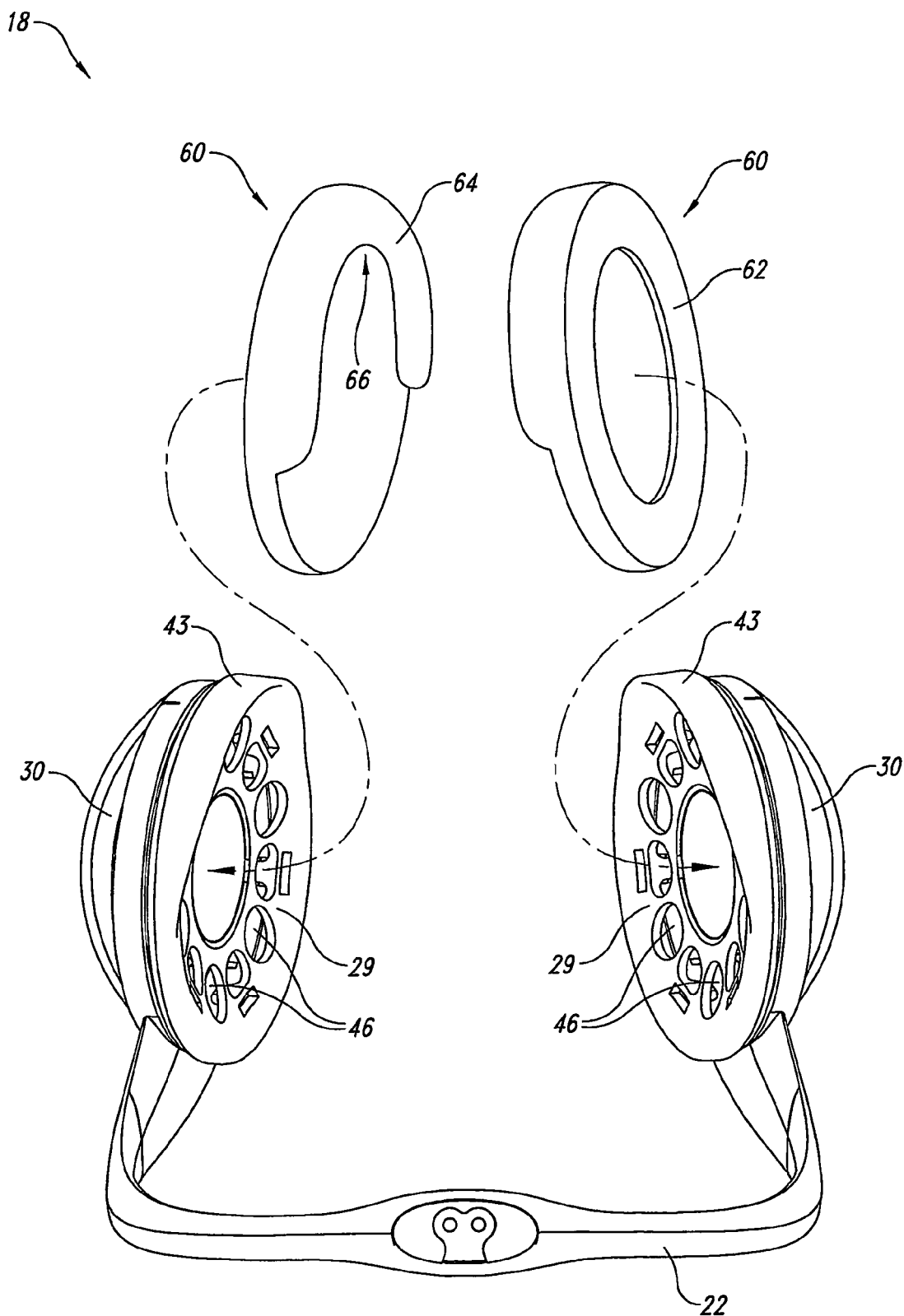
FIG. 6 is a rear view of the ear protection device of FIG. 3.

In one embodiment a material, such as fabric, is used to form ear pads 60. As shown in FIG. 6, the ear pad 60 is sized and shaped to stretch over, attach to, and cover each ear cup 28. As shown therein, the ear pad 60 has an elastic ring 62 formed on one side that slips over the ear cup 28. By design, the ear pads 60 require minimal fabric and therefore reduce the amount of fabric and related sewing required for construction.

The ear pads 60 include a component to support the device 18 on the top of the ear. As shown in FIG. 6, the component comprises an ear pocket 64 that is formed along a portion of the ear pad 60 to have an opening 66 sized and shaped to slide over the top of the user's ear. When so positioned, the pocket 64 supports the device 18 on the ear of the user.

The ear cups 28 have a ledge or protrusion 44 extending outward over the inside surface 29 to aid in supporting the device on the user's ears and to hold the pocket 64 open. Each protrusion 44 has a semi-circular shape and is formed on the upper rim 43 of the inside surface 29 of each ear cup 28. When fabric is used for the ear pads 60, the protrusions 44 work to keep ear pocket 62 on the ear pad 60 held in an opened configuration to facilitate slidable engagement with the top of the user's ear.

Referring to FIG. 3, the ear cups 28 slide into the ear frames 26 and are firmly bonded through interlocking joints (not shown) in the ear cups 28, which slot and attach into keyed joints in the ear frame 26. Alternately, attachment can be accomplished through a known process such as gluing or ultrasonic welding. In the case where an insulating material, such as fabric, is used for the ear pad 60, and when the outer ear frame 26 is fused to the concave ear cup 28, the fabric may be captured and secured between the ear frame 26 and the ear cups 28 to prevent the material from coming off.

The ear protection device 18 is firmly attached to the head 12 through the combination of the interior ear rests 44, with the ear pads 60 and the ear pockets 64 that rest on top of the user's ears, thus supporting the weight of the ear protection device 18. In embodiments where weight is a factor, the headband 22 can be formed to assist in holding the device 18 to the user's head 12. When combined, the ear pocket 64 resting on top of the ear and the resilience of the headband frame 22 can work together to ensure stability in wearing the ear protection device 18. Ideally, the resilience of the headband frame 22 does not tightly squeeze the ear protectors 23 tightly to the user's head 12. Rather, it positions the ear protectors 23 over the ears and against the hear 12 only with enough force to prevent wind from entering the user's ears.

The ear cups 28 have an interior concave shape to follow the raised shape of the user's ear to keep the ear protection device 18 in a comfortable stable position. The ear cups 28 are formed from the same lightweight material used to construct the headband 22 or from a lightweight material such as elastomer that is softer and more flexible than that of the headband 22 so as not to be affected by the individual differences in the shapes of ears and so as to help alleviate the load when ear protection device 18 is worn. Ideally, the ear protection device 18 is formed of a flexible and resilient material, such as polypropylene.

In another embodiment, the ear protection device 18 can include at least one acoustically designed component that facilitates hearing. More particularly, a passive amplifier is provided that facilitates the travel of sound waves through the ear protectors 23 and into the ear, allowing for hearing to be enhanced and minimally obstructed. In one embodiment, the device 18 includes a cover or door 30 formed on the exterior of the ear frame 26 to selectively cover and uncover a hollow interior formed between the ear frame 26 and the ear cup 28. Sound waves are directed through the ear frame 26 and holes 46 formed in the ear cups 28 and into the ear. The door 30 has a concave shape that captures the sound waves and directs them through the holes 46 formed of varying sizes in the ear cups 28.

Figure 7:
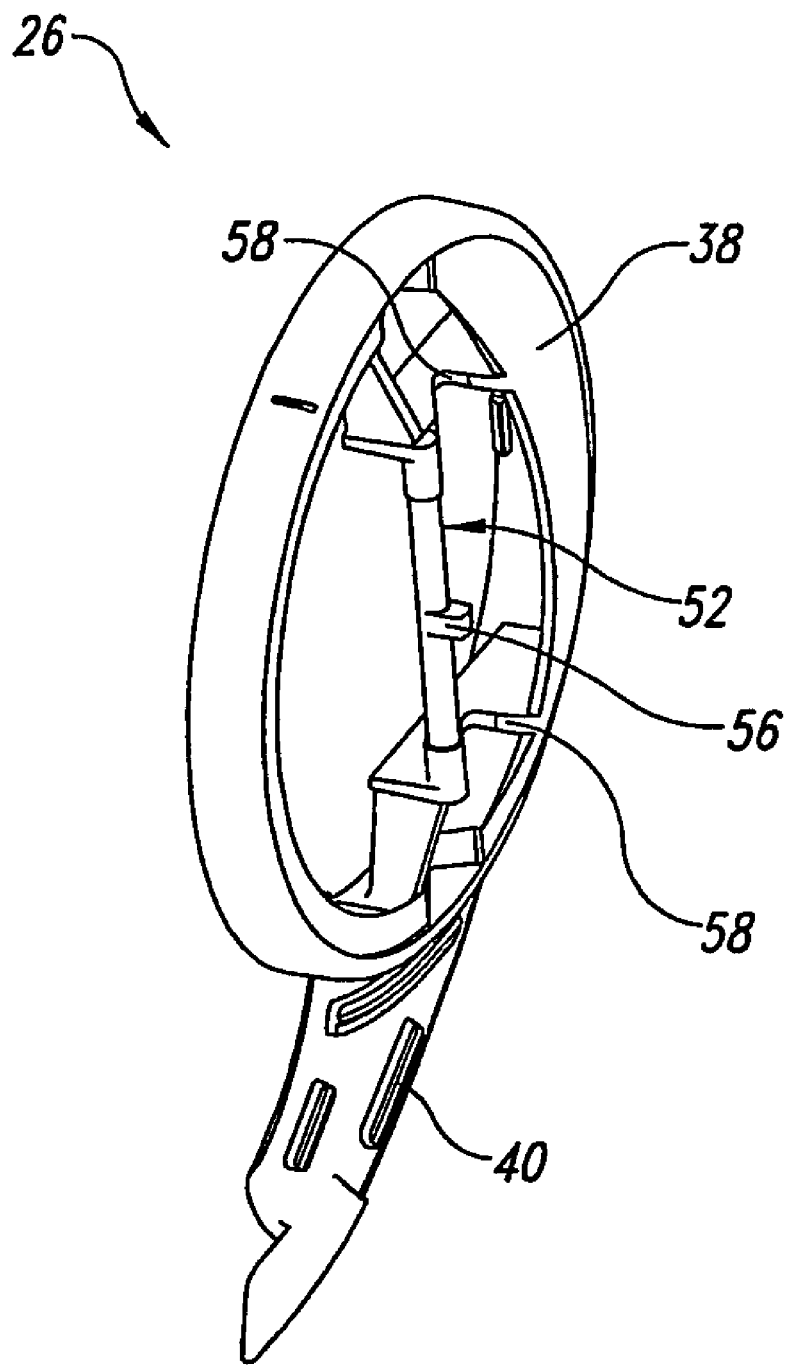
FIG. 7 is an exploded isometric projection of an outer ear frame.

The door 30 may be mounted in a variety of ways to the ear frame 26. As shown in FIGS. 7 through 8A-E, the door 30 is secured with at least one hinge 32 that is built into the ear frame 26. The design of the hinge 32 enables selective positioning of the door 30 at predetermined degrees of opening (see FIG. 4). The hinge 32 is built into the ear frame 26 and features a cylindrical post 52 onto which the door 30 is attached with at least one U-shaped cut 54 (shown in FIGS. 8C and 8D). The cylindrical post 52 varies in diameter near the top and bottom thereof so as to keep the U-shaped cuts 54 in position and prevent them from sliding. The outer ear frame 32 also features a friction lock 58 that allows the door 30 to stay partially opened, and a positive stop in the form of a nob 56 on the post 52 that enables the door 30 to stay completely open at a set position while preventing the door 30 from being pushed in further than desired.

Figure 9:
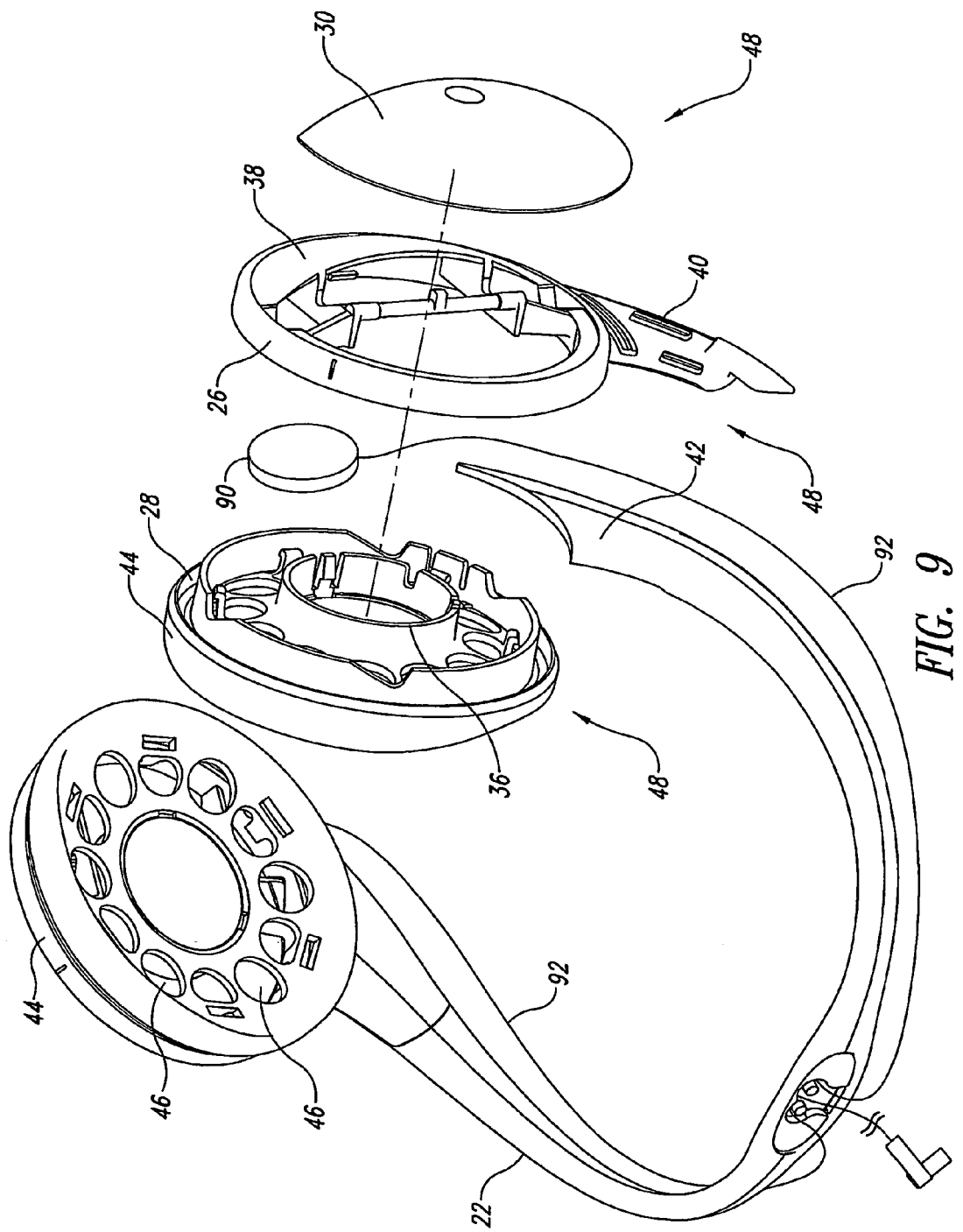
FIG. 9 is an exploded isometric view of an acoustic component assembled into the ear protection device.

Within the ear cups 28 there can be provided a housing 36, as shown in FIG. 9, as a means for mounting an acoustical device 90, such as speakers or a hearing aid or amplifier. An electrical cord 92, may be connected to the acoustic device 90, which is fastened in the acoustic housing 36 of the ear cups 28. The electrical cord 92 then passes within a groove (not shown) built into the headband frame 22 so as to hide the electrical cord 92.

In use, the ear protection device 18 is put on an individual's head 12 in the following manner: The user takes hold of the device 18 so as to slightly widen the gap between the left and right ear protectors 23 while sandwiching the head 12 so that the pockets 64 are positioned in alignment over the user's ears.

When the ear cups 28 come into contact with the top side of the ears, the user then releases the ear protection device 18, which has been pushed slightly downwards so that the ear pockets 92 come into contact with and are received over the top of the ears. In doing so, the complete device 18 is positioned on and supported by the ears. The putting on of the ear protection device 18 is then complete (see FIG. 2). If desired, the headband 22 can be formed to urge the ear protectors 23 against the user's head to prevent wind from entering the user's ears.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. For example, a sliding door can be used to selectively cover and uncover the holes 46. The embodiment of the ear protection device 18 has been described as having separate components; however the components of the ear protection device can be integrally formed as a single unitary element. Accordingly, the invention is not limited except as by the appended claims.

The invention claimed is:

1. An ear protection device, comprising:
   a pair of ear protectors, each ear protector comprising an ear cup sized and shaped to be received over a user's ear, and a pocket associated with the ear cup that is sized and shaped to be received over the top of the user's ear and to support the device on the ear, wherein each ear protector further comprises an inside wall configured to bear against the user's ear, an outside wall adjacent the inside wall and separated by a hollow interior, a first opening formed in the inside wall communicating with the hollow interior and a second opening formed in the outside wall and communicating with the hollow interior, the ear protector further comprising a cover hingedly attached to the outside wall to selectively cover and uncover the second opening formed in the outside wall; and
   a band connected to the pair of ear protectors, the band comprising resilient material and configured to hold the ear protectors apart in alignment with the user's ears and with the pockets positioned over the tops of the respective ears wherein the cover is configured to swing outward and forward to an opened position and to swing inward and coplanar with the outside wall to a closed position.

2. The device of claim 1 wherein the band is sized and shaped to extend downward below the user's earlobe when worn by the user and to extend behind the user's head to leave an unobstructed space adjacent the top of the user's ear to accommodate headgear, including glasses and hats.

3. The device of claim 1 wherein the band is configured to provide tension to hold the ear protectors against the user's head with only sufficient force to resist the entry of wind into the user's ear.

4. The device of claim 1, further comprising an electronic speaker positioned in at least one of the ear protectors.

5. The device of claim 1 wherein the ear cup is formed to have a concave shape to follow the raised shape of the user's ear.

6. The device of claim 1 wherein the pocket is formed of fabric material attached to the ear cup.

7. The device of claim 6 wherein the pocket is held in an opened configuration to facilitate slidable engagement with the top of the user's ear.

8. The device of claim 7 wherein each ear protector comprises a ledge formed thereon that is configured to hold the pocket in the opened configuration.

9. The device of claim 1, further comprising an opening formed in the ear cup to facilitate the communication of sound into the user's ear from an exterior of the ear cup, and further comprising a cover hingedly attached to the ear cup to selectively swing between an opened configuration wherein the opening in the ear cup is substantially unobstructed, and a closed position wherein the opening in the ear cup is substantially covered.

10. A device for protecting the ears of a user, the device comprising:
    means for covering the ears, the covering means comprising means for supporting the covering means on the top of the user's ears;
    means for positioning the covering means over the ears with the supporting means in alignment with the top of the user's ears; and
    means for selectively covering and uncovering an opening in the ear covering means to facilitate the hearing of the user when the selective covering means is configured to swing outward and forward to an opened position wherein the opening in the ear covering means is unobstructed.

11. The device of claim 10 wherein the positioning means is configured for urging the ear covering means against the user's head while leaving the area above the user's ear unobstructed.

12. The device of claim 10 wherein the supporting means comprises a pocket means having an opening sized and shaped to accommodate the top of the user's ear.

13. The device of claim 12 further comprising means for holding the pocket means in the opened configuration, the holding means formed on the ear covering means.

14. The device of claim 13 wherein the positioning means is configured to pass below the user's earlobes and behind the user's head to facilitate the use of headgear on the user's head.

15. An ear protection system, comprising a band having integrally formed ear protectors on first and second ends thereof, the band configured to position the first and second ear protectors in contact with the respective ears of the user with sufficient force to hold the ear protectors against the user's head and reduce the entry of wind into the user's ears, the band configured to extend downward below the earlobe of the user's ear and behind the user's head;
    each ear protector sized and shaped to substantially cover the respective ear of the user, each ear protector further comprising an ear cup having a substantially concave shape to bear against the user's ear, and an ear frame attached to the ear cup and having an outer wall to define a hollow interior between the outer wall and the ear cup, the ear cup having an opening to provide communication between the hollow interior and the user's ear, and the outer wall having an opening to provide communication between the hollow interior and the exterior of the ear protector, the ear protector further comprising a door hingedly attached to the outer wall and configured to move between an opened position wherein the opening in the outer wall is substantially unobstructed to facilitate the hearing of the user and a closed position wherein the door covers the opening in the outer wall, the door configured to swing outward and forward to deflect wind from the opening in the outer wall, and each ear protector further comprising a pocket formed on the ear cup that is sized and shaped to be slidably received over the user's ear to support the device on the top of the user's ear.

16. The system of claim 15 wherein the pocket is formed of fabric material and is held in an opened configuration by a ledge formed on the ear cup.

17. The system of claim 16 further comprising an electronic speaker positioned in at least one of the ear protectors.

18. The system of claim 16 wherein each ear protector is sized and shaped to provide unrestricted access to a space between the user's ear and the user's head to facilitate the use of headgear such as glasses and hats.

19. An ear protection device, comprising:
    a pair of ear protectors, each ear protector comprising:
        an ear cup sized and shaped to be received over a user's ear;
        a pocket associated with the ear cup that is sized and shaped to be received over the top of the user's ear and to support the device on the ear;
        an inside wall configured to bear against the user's ear;
        an outside wall adjacent the inside wall and separated by a hollow interior;
        a first opening formed in the inside wall communicating with the hollow interior;
        a second opening formed in the outside wall and communicating with the hollow interior;
        an electronic speaker positioned in at least one of the ear protectors; and
        a cover hingedly attached to the outside wall to selectively cover and uncover the second opening formed in the outside wall, wherein the cover is configured to swing outward and forward to an opened position and to swing inward and coplanar with the outside wall to a closed position; and
    a band connected to the pair of ear protectors, the band comprising lightweight resilient material and configured to hold the ear protectors apart in alignment with the user's ears and with the pockets positioned over the tops of the respective ears, the band configured to be positioned behind the user's head.

20. The device of claim 19 wherein the ear cup is formed to have a concave shape to follow the raised shape of the user's ear.

21. The device of claim 19 wherein the pocket is formed of fabric material attached to the ear cup.

22. An ear protection device, comprising:
- a pair of ear protectors, each ear protector comprising an ear cup sized and shaped to be received over a user's ear, and a pocket associated with the ear cup that is sized and shaped to be received over the top of the user's ear and to support the device on the ear;
- an opening formed in the ear cup to facilitate the communication of sound into the user's ear from an exterior of the ear cup;
- a cover hingedly attached to the ear cup to selectively swing outward and forward between an opened configuration wherein the opening in the ear cup is substantially unobstructed, and a closed position wherein the opening in the ear cup is substantially covered; and
- a band connected to the pair of ear protectors, the band comprising lightweight resilient material and configured to hold the ear protectors apart in alignment with the user's ears and with the pockets positioned over the tops of the respective ears, the band configured to be positioned behind the user's head.

23. The device of claim 22, further comprising an electronic speaker positioned in at least one of the ear protectors.

24. The device of claim 22 wherein the ear cup is formed to have a concave shape to follow the raised shape of the user's ear.

25. The device of claim 22 wherein the pocket is formed of fabric material attached to the ear cup.

\* \* \* \* \*